US007804970B2

(12) United States Patent
Hippe et al.

(10) Patent No.: US 7,804,970 B2
(45) Date of Patent: Sep. 28, 2010

(54) ARRAY INTERCONNECT FOR IMPROVED DIRECTIVITY

(75) Inventors: Rick Hippe, Snohomish, WA (US); Wei Li, Bothell, WA (US); Allan Coleman, Edmonds, WA (US)

(73) Assignee: SonoSite, Inc., Bothell, WA (US)

( * ) Notice: Subject to any disclaimer, the term of this patent is extended or adjusted under 35 U.S.C. 154(b) by 1374 days.

(21) Appl. No.: 11/257,383

(22) Filed: Oct. 24, 2005

(65) Prior Publication Data

US 2007/0093715 A1 Apr. 26, 2007

(51) Int. Cl.
*H04R 25/00* (2006.01)
*A61B 8/14* (2006.01)

(52) U.S. Cl. ........................ 381/191; 310/334; 367/153

(58) Field of Classification Search .................. 381/91, 381/92, 95, 122, 356–358, 387, 111–117, 381/190–191; 310/334; 600/437, 459; 257/734; 367/129, 137, 138, 140, 153–156
See application file for complete search history.

(56) References Cited

U.S. PATENT DOCUMENTS

| | | | | |
|---|---|---|---|---|
| 4,404,489 | A * | 9/1983 | Larson et al. | 310/334 |
| 5,267,221 | A * | 11/1993 | Miller | 367/140 |
| 5,651,365 | A | 7/1997 | Hanafy et al. | |
| 6,043,590 | A * | 3/2000 | Gilmore | 310/367 |
| 6,104,126 | A * | 8/2000 | Gilmore | 310/334 |
| 6,618,206 | B2 | 9/2003 | Tarakci et al. | |
| 6,663,567 | B2 | 12/2003 | Ji et al. | |
| 6,685,645 | B1 | 2/2004 | McLaughlin et al. | |
| 6,733,455 | B2 | 5/2004 | Mo et al. | |
| 6,773,399 | B2 | 8/2004 | Xi et al. | |
| 6,866,631 | B2 | 3/2005 | McLaughlin et al. | |
| 6,866,632 | B1 | 3/2005 | Chou et al. | |
| 6,896,658 | B2 | 5/2005 | Ji et al. | |
| 6,909,354 | B2 * | 6/2005 | Baker et al. | 338/47 |
| 6,936,008 | B2 | 8/2005 | Tarakci et al. | |

(Continued)

FOREIGN PATENT DOCUMENTS

DE 3621945 A1 1/1988

(Continued)

OTHER PUBLICATIONS

International Search Report and Written Opinion issued for PCT Application PCT/US2006/040900; Mail Date: Feb. 7, 2008; 13 Pages.

*Primary Examiner*—Xu Mei
(74) *Attorney, Agent, or Firm*—Fulbright & Jaworski L.L.P.

(57) ABSTRACT

Systems and methods which improve the directivity of a transducer array by reducing electrical cross-talk between conductors connected to individual transducer array elements through the use of a plurality of interconnect circuits are shown. A plurality of signal transmission path circuits, such as circuit boards, flexible printed circuits, etc., are used to provide electrical power to and receive signals from transducer elements of a transducer array. Embodiments couple transducer elements to conductive traces of the signal transmission path circuits in a manner such that adjacent transducer elements are not connected to conductive traces on the same signal transmission path circuit. In some embodiments, a plurality of signal transmission path circuits are offset such that two identical signal transmission path circuits can be used to provide connectivity to array transducer elements using more widely spaced conductive traces, thus reducing electrical cross-talk effects.

19 Claims, 3 Drawing Sheets

U.S. PATENT DOCUMENTS

| | | | | |
|---|---|---|---|---|
| 6,980,419 | B2 | 12/2005 | Smith et al. | |
| 7,375,420 | B2 * | 5/2008 | Fisher et al. | 257/686 |
| 7,427,825 | B2 * | 9/2008 | Frey et al. | 310/366 |
| 2003/0004414 | A1 | 1/2003 | McLaughlin et al. | |
| 2005/0131294 | A1 | 6/2005 | Ji et al. | |

FOREIGN PATENT DOCUMENTS

| | | |
|---|---|---|
| DE | 2003/1022423 | 1/2003 |
| JP | 63212299 | 5/1988 |
| JP | 06105396 | 4/1994 |
| WO | WO-2005/053863 | 6/2005 |

* cited by examiner

ARRAY INTERCONNECT FOR IMPROVED DIRECTIVITY

TECHNICAL FIELD

The invention relates to ultrasonic transducers and in particular to ultrasonic transducer arrays comprising a plurality of flex circuit connectors to improve directivity.

BACKGROUND OF THE INVENTION

Ultrasonic systems transmit ultrasonic energy into a subject and receive reflected ultrasonic energy from the subject. Such ultrasonic systems can process received energy and generate an image for analysis by a user. Accordingly, ultrasonic systems are frequently used in medical diagnostic procedures to provide detailed images of internal organs and body structures. For example, the use of ultrasonic systems allows a surgeon to search for tumors, sparing patients the discomfort and inconvenience of invasive exploratory surgery. Ultrasonic systems are also familiar to many parents as the devices that provided the first pictures of their developing children in-utero.

Such ultrasonic systems generally include a transducer array with a number of individual transducer elements arranged in a predetermined geometry in one or two dimensions. Piezoelectric materials, generally of ceramic or polymeric material, convert between electrical energy and acoustic energy and are often used to form individual transducer elements. A multi-element transducer array is generally formed from a strip of such piezoelectric material, which is then cut to form a row or rows of individual transducer elements.

Ultrasonic systems that use transducer arrays with large numbers of individual transducer elements are generally desirable as providing a large viewing field, a large signal aperture, and/or to provide desired beam forming. Typically, as the density of individual transducer elements of a transducer array increases, so does the image quality produced by a system using that transducer array. However, as the density of the transducer array increases, the pitch of the transducer array, or the longitudinal distance of individual transducer elements, decreases. In conventional transducer arrays, a small transducer array pitch can result in undesirable interference between elements in the form of electrical and acoustic interactions, and image quality can suffer due to such cross-talk. Cross-talk can occur at the transducer and also in transmission circuitry contained in a transducer array head. As a transducer array becomes more dense, so too do connectors providing electrical connections to the transducer array, conductive circuits on printed circuit boards, and other transmission apparatus connected to the array. If the pitch between conductive circuits becomes too small, undesirable electrical cross-talk increases.

Various ultrasonic systems have employed transducer arrays wherein transducer elements are disposed in a two-dimensional configuration. That is, a plurality of transducer elements are disposed along the long or longitudinal axis of the transducer array and a plurality of transducer elements along the width or lateral axis of the transducer array. Such two-dimensional transducer arrays typically assume a configuration in which separate signal transmission path circuits are each coupled to a parallel set of transducer elements. To the inventors' knowledge, such two-dimensional arrays have not been used to address the foregoing transducer element density issues or to provide improved directivity, but rather have been to provide a transducer array configuration adapted for use in particular situations.

BRIEF SUMMARY OF THE INVENTION

The present invention is directed to systems and methods which improve the directivity of a transducer array by reducing electrical cross-talk between conductors connected to individual transducer array elements through the use of a plurality of interconnect circuits. Improved directivity transducer arrays allow ultrasonic systems to generate more detailed images of desired targets.

Certain embodiments of the present invention reduce the density of conductor traces electrically connected to transducer elements of a transducer array. A plurality of signal transmission path circuits, such as circuit boards, flexible printed circuits, etc., are used according to embodiments of the invention to provide electrical power to and receive signals from transducer elements, such as may comprise piezoelectric transducer elements, of a transducer array. The signal transmission path circuits comprise one or more conductive traces. Each conductive trace is coupled to one of the transducer array elements. In embodiments of the present invention, transducer elements are coupled to conductive traces in a manner such that adjacent transducer elements are not connected to conductive traces on the same signal transmission path circuit.

In some embodiments of the present invention, a plurality of signal transmission path circuits are offset in a direction that allows the first conductive trace on one circuit to connect to the first transducer element on an array. The offset is such that the first conductive trace on a second signal transmission path circuit connects to the second transducer element on an array. In this manner, two identical signal transmission path circuits can be used to provide connectivity to array transducer elements using more widely spaced conductive traces, thus reducing electrical cross-talk effects.

Embodiments of the present invention are advantageously used with one-dimensional transducer element arrays in a transducer head. A plurality of offset signal transmission path circuits is embedded in a matrix material. The matrix material has a precision surface (which can be flat, cylindrical, or other shape) for receiving the transducer element array. A manufacturing process also exposes conductive trace ends present on the signal transmission path circuits. These exposed ends form a two-dimensional staggered array, again allowing a low density conductive trace signal transmission path circuit to be used, reducing electrical cross-talk.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
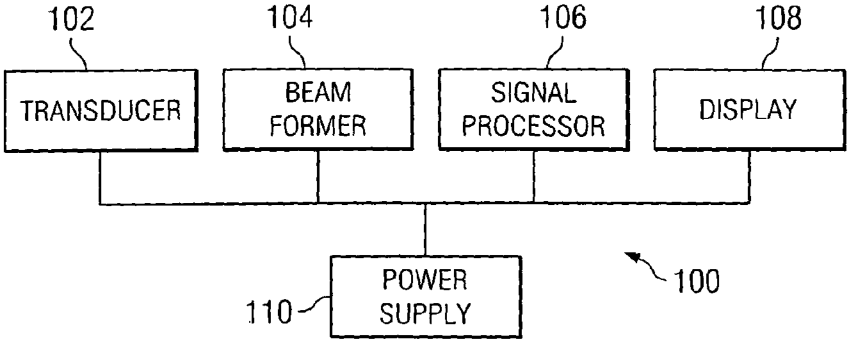
FIG. 1 is a block diagram of an ultrasonic diagnostic instrument and transducer array according to an embodiment of the present invention.

FIG. 1 is a block diagram of an ultrasonic diagnostic instrument 100 in which embodiments of the present invention may be employed. Ultrasonic transducer array 102 generates ultrasonic sound waves and receives reflected ultrasonic sound waves. Transducer array 102 comprises a number of individual transducer elements that varies depending on the desired application. In a preferred embodiment, a transducer array is a flat linear array similar to transducer array 102 shown in FIG. 1. However, in other embodiments, a transducer array may be curved, non-linear, or other configuration. Transducer array 102 comprises a one-dimensional array. That is, transducer array 102 comprises a plurality of transducer elements disposed along the long or longitudinal axis of the transducer array and one transducer element along the width or lateral axis of the transducer array (it being appreciated that a two-dimensional array would, in contrast, comprises a plurality of transducer elements disposed along the long or longitudinal axis of the transducer array and a plurality of transducer elements along the width or lateral axis of the transducer array).

Beamforming comprising in some embodiments ultrasonic wave generation and echo signal processing is accomplished by beamformer circuitry 104 which interfaces with the transducer 102. Signal information from beamformer circuitry 104 is received by signal processor 106 which processes the signal information. Signal processor 106 drives display 108 thereby producing visible information used by a user. Power supply 110 provides electrical power used by components of ultrasonic diagnostic instrument 100. Preferred embodiments of the present invention use a battery for power supply 110.

Figure 2:
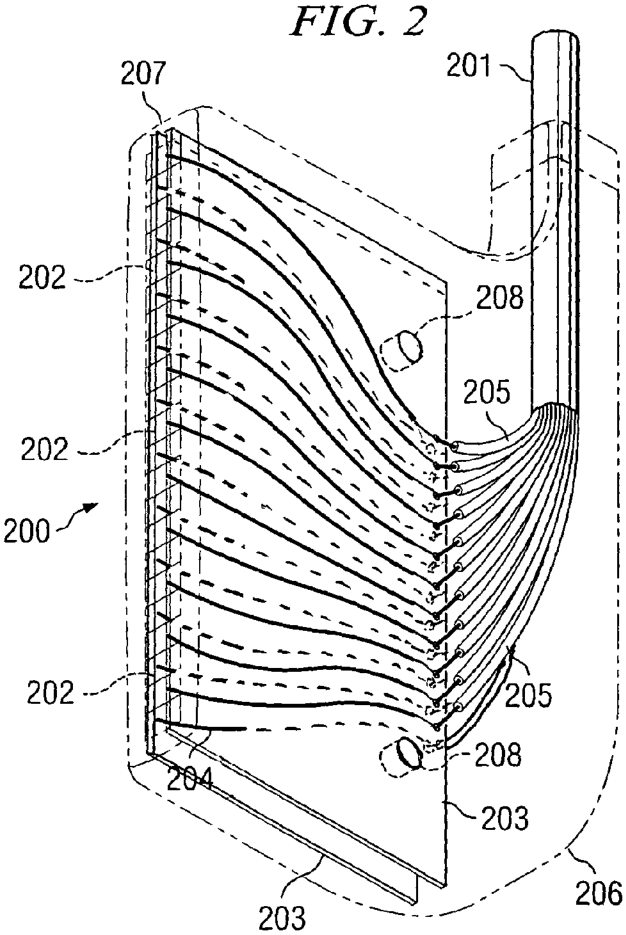
FIG. 2 is an illustration of a transducer assembly having a transducer array and flexible circuits adapted according to an embodiment of the invention.

FIG. 2 is an illustration of a transducer array used in a hand-held transducer assembly adapted according to an embodiment of the present invention. Transducer assembly 200 is comprised of a body 206. Signal cable 201 enters body 206 at one end and is routed into the interior of body 206. Transducer assembly further comprises a linear piezoelectric transducer array 207 comprising a number of individual transducer elements 202. In certain embodiments of the present invention, curved transducer arrays may be used. In a preferred embodiment of the present invention, transducer array 207 comprises 128 transducer elements. However, in other embodiments of the invention, different quantities of transducer elements 202 are present. Individual transducer elements 202 are electrical coupled to conductive traces 204 on one of two flexible printed circuits (FPCs) 203 such that adjacent transducer elements 202 are connected to a conductive trace 204 on a different one of FPCs 203. While many of the embodiments of the present invention described herein are shown with FPCs, standard printed circuit boards, flexible circuits or other media for providing the appropriate signal can also be used with certain embodiments.

Returning to FIG. 2, each FPC 203 is connected to a separate cable bundle 205 which merges into signal cable 201. While this embodiment of the present invention utilizes two FPCs to divide electrical connections to transducer elements 202, more FPCs can be used to further divide the electrical connections to transducer elements. Transducer assembly 200 further comprises two dowel pins 208 attached to body 206. Holes in FPCs 203 (not shown) are sized to receive tooling features (in this embodiment, dowel pins 208) which project through the holes to accurately position FPCs 203 in a desired position relative to each other.

Figure 3:
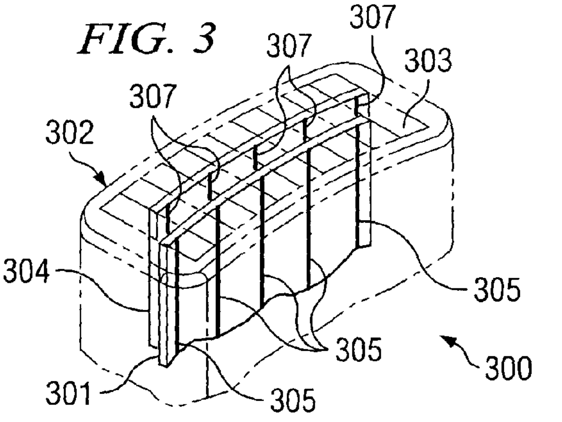
FIG. 3 is an illustration of a backing block comprising a one-dimensional curved transducer array and flexible circuits adapted according to an embodiment of the present invention.

FIG. 3 is an illustration of a backing block 300 comprising a one-dimensional curved transducer array 302 coupled to offset FPCs 301, 304 according to an embodiment of the present invention. Offset FPCs are separated vertically and offset by the pitch of the array along the long or longitudinal axis of the transducer array. The short or lateral axis of a transducer array is generally along the width of a transducer element of the transducer array.

While this embodiment uses a curved transducer array 302, in other embodiments, transducer array 302 can assume other forms, such as, for example, a linear form. In this embodiment, a first FPC 301 is used to couple conductive traces 305 to individual transducer elements 303 located in transducer array 302. Conductive traces 305 from first FPC 301 are coupled alternatingly to non-adjacent transducer elements 303. A second FPC 304 has conductive traces 307 coupled to non-adjacent transducer elements 303 that are not already connected to first FPC 301. FPCs are generally formed from a flexible sheet of nonconductive material such as Kapton. Conductive traces 301 are then formed on the nonconductive material using techniques such as etching, photolithography, or electroplating. Conductive traces 301 are themselves formed of conductive material such as, for example, copper.

In this embodiment first FPC 301 and second FPC 304 are nearly identical. To manufacture backing block 300 in one embodiment, first FPC 301 and second FPC 304 are positioned in a mold with an offset along the long axis of the transducer array as described above. In other embodiments, FPCs may not be identical and may comprise additional features or structures not present in the other FPC. The offset FPCs are then encased with a matrix material forming backing block 300. The formed backing block may be cured and/or processed to form a desired shape or to expose electrical connections. Once electrical connections are exposed, transducer elements 303 can be positioned on the exposed electrical connections. Cables or other electrical transmission components may be attached at connector end 308 of backing block 300 in certain embodiments of the present invention. The reduced number of traces on each FPC provides not only advantageous imaging performance and directivity, but also allows for connecting cables to be split or otherwise formed in bundles that allows the formation of transducer assemblies in shapes not easily obtained with conventional systems. For example, two smaller cable bundles used in certain embodiments of the present invention can allow a transducer assembly to have more flexibility and/or a narrower cross-section.

While the embodiment of the present invention shown in FIG. 3 comprises a transducer array with ten transducer elements, in other embodiments, more or fewer transducer elements are present. In a preferred embodiment, 128 individual transducer elements are present.

Also, FPCs may comprise material that is used to shield conductive traces 305, 307 from interference (crosstalk). In certain embodiments, grounding conductive material such as copper is affixed to the side of an FPC not occupied by conductive traces. The grounding material can be placed on only one side of an FPC or can also extend around the FPC, thereby shielding conductive traces 305, 307 from interference on all sides. The grounding material is positioned to shield conductive traces 305, 307 while not presenting a profile that will generate an acoustic signal while the array is operating.

Figure 4:
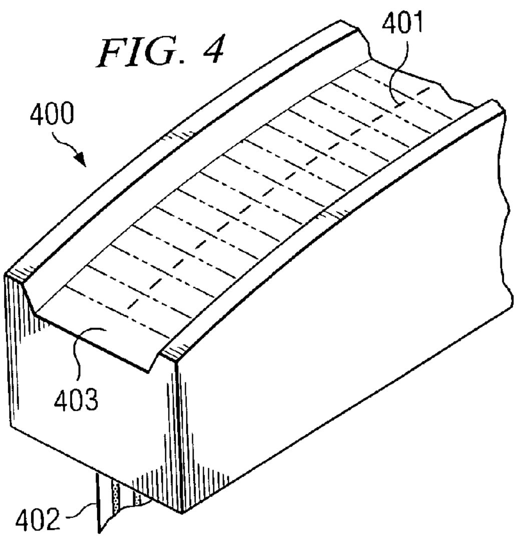
FIG. 4 shows a conventional backing block formed with a single flexible circuit and a one-dimensional array of exposed conductive traces.

FIG. 4 shows a conventional backing block 400 with one row of exposed conductive traces 401 in a curved transducer assembly. As earlier mentioned, in other embodiments a flat linear transducer assembly or other transducer configuration may be used. Exposed conductive traces 401 are part of a single FPC 402 embedded in a matrix material forming backing block 400. Individual transducer array elements (not shown) may be attached to surface 403, a precision surface on backing block 400 with a single exposed conductive trace 401 contacting each individual transducer array element.

Figure 5A:
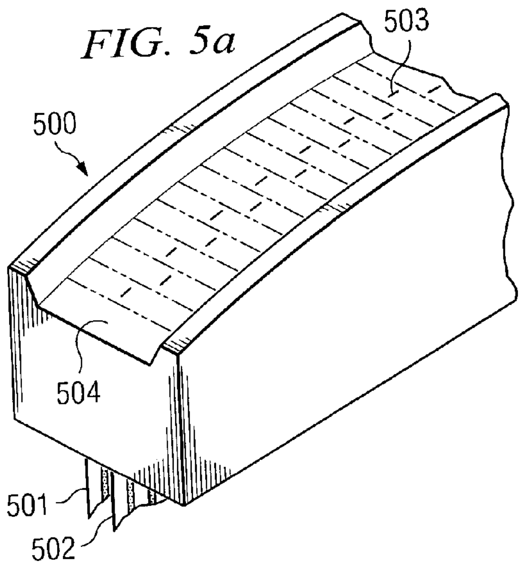
FIGS. 5*a*-5*c* are illustrations of backing blocks according to embodiments of the present invention.
Figure 5B:
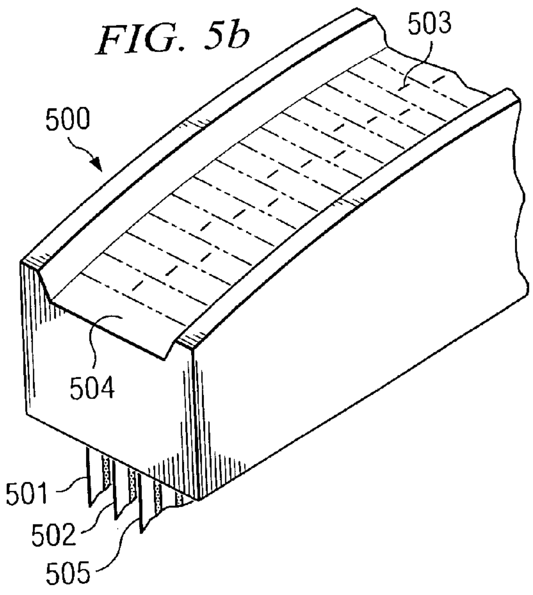

FIGS. 5*a* and 5*b* are illustrations of backing blocks according to embodiments of the present invention. FIG. 5*a* shows backing block 500 comprising two FPCs 501, 502 embedded in a matrix material. The FPCs are offset in both a vertical plane and in a plane formed by a long axis of the transducer array, and are offset along the long axis by the pitch of the transducer array. In other embodiments of the present invention, the offsets of FPCs may be different. The matrix material has been processed to form groove 504 with two rows of exposed conductive traces 503. Individual transducer array elements (not shown) may be inserted in a one-dimensional array in groove 504. Individual transducer array elements thus inserted each contact a single exposed conductive trace. Adjacent individual transducer array elements contact exposed conductive traces that are positioned on different FPCs. For example, a transducer array element placed on the first transducer element at the front of the illustration contacts an exposed conductive trace of FPC 501. A transducer array element placed in the position adjacent to the first would contact an exposed conductive trace of FPC 502. Additional transducer elements placed would continue to alternate between contacting exposed conductive traces of different FPCs. In this way, conductive traces are alternatingly connected electrically to individual transducer elements.

Figure 5C:
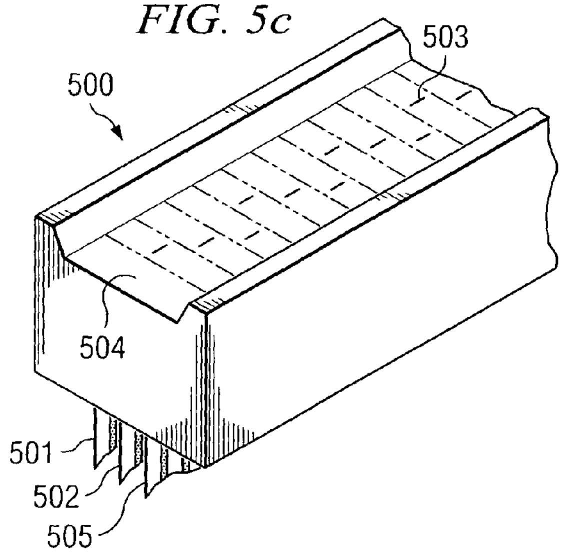

FIG. 5*b* shows backing block 500 comprising three FPCs 501, 502, and 505 embedded in a matrix material. As with the two FPC backing block shown in FIG. 5*a*, groove 504 has three rows of exposed conductive traces 503 that contact individual transducer array elements (not shown) inserted in groove 504. In the illustrated embodiment, inserted individual transducer array elements alternate between the three FPCs. For example, a transducer array element placed on the first transducer element at the front of the illustration contacts an exposed conductive trace of FPC 501. A transducer array element placed in the position adjacent to the first would contact an exposed conductive trace of FPC 502. And a third transducer array element placed in the next position would contact an exposed conductive trace of FPC 505. This pattern repeats for additional transducer array elements added to groove 504. Other embodiments of the present invention may have backing blocks comprising more than three FPCs. FIG. 5*c* is a flat linear version of the embodiment shown in FIG. 5*b*.

Figure 6:
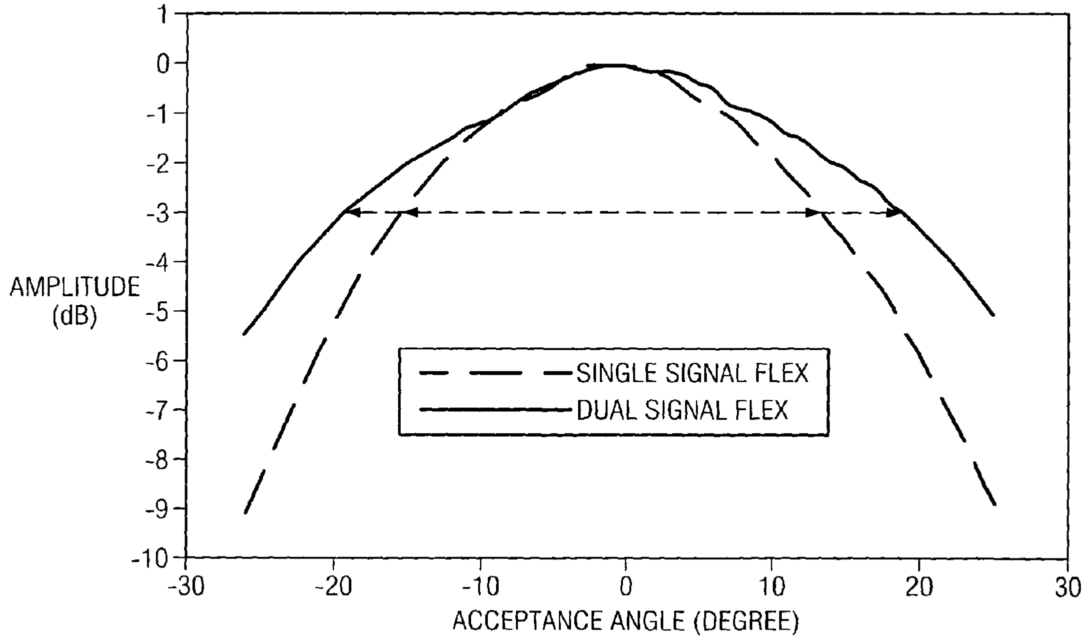
FIG. 6 is a graph showing the directivity of an embodiment of the present invention compared to a conventional transducer array.

Improved directivity of transducer arrays according to embodiments of the present invention is noted compared to conventional transducer arrays. FIG. 6 shows a exemplary graph illustrating the results of a directivity test comparing a conventional one-dimensional linear array with a single FPC similar to the one shown in FIG. 4 to the one-dimensional linear array with a dual FPC similar to the one shown in FIG. 5*a*. The dual FPC transducer array configuration according to an embodiment of the present invention had a measured acceptance angle (at a −3 dB cutoff) of approximately 38 degrees compared to a measured acceptance angle of 29 degrees for the conventional transducer array. This represents an increase of approximately 30 percent for an embodiment of the present invention compared to a conventional transducer array. In other embodiments, greater or lesser increases in directivity may be found depending on factors such as number of FPCs used, array type, array size, transducer element pitch, operating frequency, etc.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method for improving the directivity of an acoustic transducer array comprising:

providing a transducer comprising a plurality of transducer elements in a one-dimensional array;

providing a plurality of signal transmission path circuits, each signal transmission path circuit comprising at least one conductive trace, said signal transmission path circuits positioned adjacent to said transducer elements;

forming a backing block of a matrix material and machining said matrix material to expose conductive trace material of said conductive traces;

coupling a first group of non-adjacent transducer elements of said transducer elements to conductive traces of a first signal transmission path circuit of said plurality of signal transmission path circuits; and coupling a second group of non-adjacent transducer elements of said transducer elements to conductive traces of a second signal transmission path circuit of said signal transmission path circuits.

2. The method of claim 1 wherein said signal transmission path circuits comprise flexible circuits.

3. The method of claim 2 wherein said flexible circuits are flexible printed circuits.

4. The method of claim 1 wherein said transducer comprises a curved transmit/receive head.

5. The method of claim 1 wherein said transducer comprises a linear transmit/receive head.

6. The method of claim 1 wherein said providing a plurality of signal transmission path circuits comprises providing a plurality of flexible circuits that are offset relative to each other along the long axis of said transducer array.

7. The method of claim 1 wherein said providing a plurality of signal transmission path circuits comprises providing a plurality of substantially identical flexible circuits.

8. The method of claim 1 wherein said providing a plurality of signal transmission path circuits comprises providing a plurality of flexible circuits comprising a ground plane.

9. A method for improving the directivity of an acoustic transducer array comprising:

providing a transducer comprising a plurality of transducer elements in a one-dimensional array;

providing a plurality of signal transmission path circuits, each signal transmission path circuit comprising at least one conductive trace, said signal transmission path circuits positioned adjacent to said transducer elements;

coupling a first group of non-adjacent transducer elements of said transducer elements to conductive traces of a first signal transmission path circuit of said plurality of signal transmission path circuits;

coupling a second group of non-adjacent transducer elements of said transducer elements to conductive traces of a second signal transmission path circuit of said signal transmission path circuits; and coupling a third group of non-adjacent transducer elements of said transducer elements to conductive traces of a third signal transmission path circuit of said signal transmission path circuits.

10. A method for improving the directivity of an acoustic transducer array comprising:

providing a transducer comprising a plurality of transducer elements in a one-dimensional array;

providing a plurality of signal transmission path circuits, each transmission path circuit comprising at least one conductive trace, said signal transmission path circuits positioned adjacent to said transducer elements;

coupling a first group of non-adjacent transducer elements of said transducer elements to conductive traces of a first signal transmission path circuit of said plurality of signal transmission path circuits;

coupling a second group of non-adjacent transducer elements of said transducer elements to conductive traces of a second signal transmission path circuit of said signal transmission path circuits;

wherein said providing a plurality of signal transmission path circuits comprises providing a plurality of flexible circuits comprising at least one guide hole.

11. An acoustic transducer apparatus comprising:

a plurality of transducer elements formed in a one-dimensional array;

a plurality of flexible circuits, each flexible circuit comprising at least one conductive trace, said at least one conductive traces alternatingly coupled electrically to ones of said plurality of transducer elements such that adjacent transducer elements are coupled to conductive traces on different flexible circuits of said plurality of flexible circuits; and a backing block of matrix material, wherein said matrix material exposes conductive trace material of said at least one conductive traces.

12. The acoustic transducer apparatus of claim 11 wherein said flexible circuits are flexible printed circuits.

13. The acoustic transducer apparatus of claim 11 wherein said one-dimensional array is formed in a flat linear backing block.

14. The acoustic transducer apparatus of claim 11 wherein said one-dimensional array is formed in a curved backing block.

15. The acoustic transducer apparatus of claim 11 wherein said plurality of flexible circuits are offset relative to each other along the long axis of said array.

16. The acoustic transducer apparatus of claim 11 wherein said flexible circuits comprise a ground plane.

17. An acoustic transducer apparatus comprising:

a plurality of transducer elements formed in a one-dimensional array;

a plurality of flexible circuits, each flexible circuit comprising at least one conductive trace, said at least one conductive traces alternatingly coupled electrically to ones of said plurality of transducer elements such that adjacent transducer elements are coupled to conductive traces on different flexible circuits of said plurality of flexible circuits;

wherein said plurality of flexible circuits comprise at least one guide hole for receiving at least one dowel pin.

18. The acoustic transducer apparatus of claim 17 wherein said flexible circuits are offset relative to each other along the long axis of said transducer array when at least one dowel pin is inserted in said at least one guide hole of said flexible circuits.

19. The acoustic transducer apparatus of claim 17 wherein said flexible circuits are substantially identical.

* * * * *